United States Patent [19]

Ishikawa

[11] Patent Number: 5,334,521

[45] Date of Patent: Aug. 2, 1994

[54] CLONING AND CHARACTERIZATION OF A CARDIAC ADENYLYL CYCLASE

[75] Inventor: Yoshihiro Ishikawa, Cresskill, N.J.

[73] Assignee: American Cyanamid Company, Wayne, N.J.

[21] Appl. No.: 793,961

[22] Filed: Nov. 18, 1991

[51] Int. Cl.⁵ .................................. C12N 15/00
[52] U.S. Cl. ......................... 435/172.1; 435/320.1; 435/252.3; 435/252.33; 536/23.2
[58] Field of Search ............... 435/232, 172.3, 320.1, 435/252.3, 69.1, 252.33, 172.1; 536/27, 23.2

[56] References Cited

PUBLICATIONS

Pfeuffer et al., PNAS vol. 82, May 1985, pp. 3086–3090.
Mollner et al, Eur. J. Biochem, vol. 71, 1988, pp. 265–271.
Bakalyar et al, Science, vol. 250, Dec. 7, 1990, pp. 1403–1406.
Krupinski et al., Science, vol. 244, Jun. 30, 1989, pp. 1558–1564.
Pfeuffer et al., "Purification of Adenylyl Cyclase from Heart and Brain," Methods in Enzymology, vol. 195, pp. 83–91 (Academic Press, Inc., N.Y. 1991).
Gao et al., "Cloning and expression of a widely distributed (type IV) adenylyl cyclase," Proc. Natl. Acad. Sci. USA 88: 10178–10182 (1991).
Homcy et al., "Affinity purification of cardiac adenylate cyclase: Dependence on prior hydrophobic resolution," Proc. Natl. Acad. Sci. USA 75(1):59–63 (1978).
Parma et al., "Sequence of a Human Brain Adenylyl Cyclase Partial cDNA: Evidence for a consensus cyclase specific domain," Biochem. Biophys. Res. Comm. 179(1):455–462 (1991).
Feinstein et al., "Molecular cloning and characterization of a $Ca^{2+}$/calmodulin–insensitive adenylyl cyclase from rat brain," Proc. Natl. Acad. Sci. USA 88:10173–10177 (1991).
Ishikawa et al., "Isolation and Characterization of a Novel Cardiac Adenylylcyclase cDNA," J. Biol. Chem. 267(19):13553–13557 (1992).
Katsushika et al., "Cloning and characterization of a sixth adenylyl cyclase isoform: Types V and VI constitute a subgroup . . . ," Proc. Natl. Acad. Sci. USA 89:8774–8778 (1992).
Yoshimura et al., "Cloning and expression of a $Ca^{2+}$–inhibitable adenylyl cyclase from NCB–20 cells," Proc. Natl. Acad. Sci. USA 89:6716–6720 (1992).
Wayman et al., "Isolation of cDNA clones for heart adenylate cyclase," FASEB J. 6(5):A1632 (Feb. 28, 1992).

Primary Examiner—Robert A. Wax
Assistant Examiner—Keith D. Hendricks
Attorney, Agent, or Firm—Estelle J. Tsevdos

[57] ABSTRACT

A DNA sequence encoding a novel effector enzyme referred to as a cardiac adenylyl cyclase is described. The amino acid sequence of the cardiac adenylyl cyclase encoded by that DNA sequence is also described.

10 Claims, 12 Drawing Sheets

```
         10        20        30        40        50        60
          *         *         *         *         *         *
CGGCCGGGCGGGCTGCGGGCGGCGAGGCTCGCCGGGGCGCGGGCGGCGGGGGGCGCGGGG 70        80        90       100       110       120
          *         *         *         *         *         *
CGGCCGGCCGGGCCGGAGCCCGGGGGGCGGCGGGGCGGGGTCCGGGGCGGCGCGGAGCGG 130       140       150       160       170       180
          *         *         *         *         *         *
GGCCGGCAGCATGTCGTGGTTTAGTGGCCTCCTGGTCCCCAAAGTGGATGAACGGAAGAC
          M  S  W  F  S  G  L  L  V  P  K  V  D  E  R  K  T>
             ↑
        190       200       210       220       230       240
          *         *         *         *         *         *
AGCCTGGGGTGAACGCAATGGGCAGAAGCGTCCACGCCGCGGGACTCGGACCAGTGGCTT
   A  W  G  E  R  N  G  Q  K  R  P  R  R  G  T  R  T  S  G  F>

250       260       270       280       290       300
          *         *         *         *         *         *
CTGCACGCCCCGCTATATGAGCTGCCTCCGGGATGCGCAGCCCCCCAGTCCCACCCCTGC
   C  T  P  R  Y  M  S  C  L  R  D  A  Q  P  P  S  P  T  P  A>

310       320       330       340       350       360
          *         *         *         *         *         *
GGCTCCCCCTCGGTGCCCCTGGCAGGATGAGGCCTTCATCCGGAGAGGCGGCCCGGGCAA
   A  P  P  R  C  P  W  Q  D  E  A  F  I  R  R  G  G  P  G  K>

370       380       390       400       410       420
          *         *         *         *         *         *
GGGCACGGAGCTGGGGCTGCGGGCGGTGGCCCTGGGCTTCGAGGACACTGAGGCCATGTC
   G  T  E  L  G  L  R  A  V  A  L  G  F  E  D  T  E  A  M  S>

430       440       450       460       470       480
          *         *         *         *         *         *
AGCGGTTGGGGCAGCTGGAGGTGGCCCTGACGTGACCCCCGGGAGTAGGCGATCCTGCTG
   A  V  G  A  A  G  G  G  P  D  V  T  P  G  S  R  R  S  C  W>

490       500       510       520       530       540
          *         *         *         *         *         *
GCGCCGTCTGGCCCAGGTGTTCCAGTCGAAGCAGTTCCGCTCGGCCAAGCTGGAGCGCCT
   R  R  L  A  Q  V  F  Q  S  K  Q  F  R  S  A  K  L  E  R  L>

550       560       570       580       590       600
          *         *         *         *         *         *
GTACCAGCGGTACTTCTTTCAGATGAACCAGAGCAGCCTGACGCTGCTGATGGCGGTGCT
   Y  Q  R  Y  F  F  Q  M  N  Q  S  S  L  T  L  L  M  A  V  L>
```

FIG. 2A

```
         610       620       630       640       650       660
          *         *         •         *         *         *
GGTGCTGCTGACAGCGGTGCTGCTAGCCTTCCATGCTGCACCTGCCCGCCCTCAGCCTGC
  V  L  L  T  A  V  L  L  A  F  H  A  A  P  A  R  P  Q  P  A>

670       680       690       700       710       720
          *         *         •         *         *         *
CTACGTGGCCCTGCTGGCCTGTGCCGCCACCCTCTTCGTGGCGCTCATGGTGGTGTGTAA
  Y  V  A  L  L  A  C  A  A  T  L  F  V  A  L  M  V  V  C  N>

730       740       750       760       770       780
          *         *         *         *         *         *
CCGGCACAGCTTTCGCCAGGACTCCATGTGGGTGGTGAGCTACGTGGTGCTGGGCATCCT
  R  H  S  F  R  Q  D  S  M  W  V  V  S  Y  V  V  L  G  I  L>

790       800       810       820       830       840
          *         *         *         *         *         *
GGCAGCCGTTCAGGTTGGGGGTGCCCTGGCAGCCAACCCCCGCAGCCCCTCTGTGGGCCT
  A  A  V  Q  V  G  G  A  L  A  A  N  P  R  S  P  S  V  G  L>

850       860       870       880       890       900
          *         *         *         *         *         *
CTGGTGCCCTGTGTTTTTTGTCTACATCACCTACACGCTCCTACCCATCCGCATGCGGGC
  W  C  P  V  F  F  V  Y  I  T  Y  T  L  L  P  I  R  M  R  A>

910       920       930       940       950       960
          *         *         *         *         *         *
AGCTGTCTTCAGTGGCCTGGGCCTGTCCACCCTGCATTTGATCTTGGCCTGGCAACTCAA
  A  V  F  S  G  L  G  L  S  T  L  H  L  I  L  A  W  Q  L  N>

970       980       990      1000      1010      1020
          *         *         *         *         *         *
CCGCGGTGACGCCTTCCTCTGGAAGCAGCTCGGTGCCAACATGCTGCTGTTCCTCTGCAC
  R  G  D  A  F  L  W  K  Q  L  G  A  N  M  L  L  F  L  C  T>

1030      1040      1050      1060      1070      1080
          *         *         *         *         *         *
CAACGTCATTGGCATCTGCACACACTACCCAGCTGAGGTCTCTCAGCGCCAGGCCTTTCA
  N  V  I  G  I  C  T  H  Y  P  A  E  V  S  Q  R  Q  A  F  Q>

1090      1100      1110      1120      1130      1140
          *         *         *         *         *         *
GGAGACCCGCGGTTACATTCAGGCCCGGCTGCACCTGCCAGATGAGAACCGGCAGCAGGA
  E  T  R  G  Y  I  Q  A  R  L  H  L  P  D  E  N  R  Q  Q  E>
```

FIG. 2B

```
      1150        1160        1170        1180        1190        1200
        *           *           *           *           *           *
ACGGCTGCTGCTGTCCGTGTTGCCCCAGCATGTTGCCATGGAGATGAAAGAAGATATCAA
  R  L  L  S  V  L  P  Q  H  V  A  M  E  M  K  E  D  I  N>

1210        1220        1230        1240        1250        1260
        *           *           *           *           *           *
CACAAAGAAAGAAGACATGATGTTCCACAAGATCTACATCCAGAAGCATGACAATGTCAG
  T  K  K  E  D  M  M  F  H  K  I  Y  I  Q  K  H  D  N  V  S>

1270        1280        1290        1300        1310        1320
        *           *           *           *           *           *
CATCCTGTTTGCAGACATTGAAGGCTTCACCAGCCTGGCGTCCCAGTGCACCGCGCAGGA
  I  L  F  A  D  I  E  G  F  T  S  L  A  S  Q  C  T  A  Q  E>

1330        1340        1350        1360        1370        1380
        *           *           *           *           *           *
GCTGGTCATGACCCTGAACGAGCTCTTCGCCCGGTTTGACAAGCTGGCTGCGGAAAATCA
  L  V  M  T  L  N  E  L  F  A  R  F  D  K  L  A  A  E  N  H>

1390        1400        1410        1420        1430        1440
        *           *           *           *           *           *
CTGCCTGAGGATCAAGATCTTAGGGGACTGTTACTACTGTGTGTCGGGGCTGCCGGAGGC
  C  L  R  I  K  I  L  G  D  C  Y  Y  C  V  S  G  L  P  E  A>

1450        1460        1470        1480        1490        1500
        *           *           *           *           *           *
CCGGGCAGACCATGCCCACTGCTGTGTGGAGATGGGGGTGGACATGATCGAGGCCATCTC
  R  A  D  H  A  H  C  C  V  E  M  G  V  D  M  I  E  A  I  S>

1510        1520        1530        1540        1550        1560
        *           *           *           *           *           *
GCTGGTGCGTGAGGTGACAGGTGTGAACGTGAACATGCGCGTGGGCATCCACAGCGGGCG
  L  V  R  E  V  T  G  V  N  V  N  M  R  V  G  I  H  S  G  R>

1570        1580        1590        1600        1610        1620
        *           *           *           *           *           *
TGTGCACTGTGGTGTCCTTGGCCTGCGGAAATGGCAGTTCGACGTGTGGTCCAATGACGT
  V  H  C  G  V  L  G  L  R  K  W  Q  F  D  V  W  S  N  D  V>

1630        1640        1650        1660        1670        1680
        *           *           *           *           *           *
GACTCTGGCCAACCATATGGAGGCGGCCCGGGCCGGCCGCATCCACATCACCCGGGCCAC
  T  L  A  N  H  M  E  A  A  R  A  G  R  I  H  I  T  R  A  T>
```

FIG. 2C

```
        1690       1700       1710       1720       1730       1740
          *          *          *          *          *          *
GCTGCAGTACCTGAACGGGGACTACGAGGTGGAGCCGGGCCGCGGTGGCGAGCGGAACGC
  L  Q  Y  L  N  G  D  Y  E  V  E  P  G  R  G  G  E  R  N  A>

1750       1760       1770       1780       1790       1800
          *          *          *          *          *          *
GTACCTCAAGGAGCAGCACATCGAGACCTTCCTCATCCTGGGAGCCAGCCAGAAACGGAA
  Y  L  K  E  Q  H  I  E  T  F  L  I  L  G  A  S  Q  K  R  K>

1810       1820       1830       1840       1850       1860
          *          *          *          *          *          *
AGAGGAGAAGGCCATGCTGGCCAAGCTGCAGCGGACGCGGGCCAACTCCATGGAAGGCCT
  E  E  K  A  M  L  A  K  L  Q  R  T  R  A  N  S  M  E  G  L>

1870       1880       1890       1900       1910       1920
          *          *          *          *          *          *
GATGCCACGCTGGGTGCCCGACCGCGCCTTCTCCCGGACCAAGGACTCCAAGGCTTTCCG
  M  P  R  W  V  P  D  R  A  F  S  R  T  K  D  S  K  A  F  R>

1930       1940       1950       1960       1970       1980
          *          *          *          *          *          *
CCAGATGGGCATTGATGATTCCAGCAAAGACAACCGGGGTGCCCAAGATGCCCTGAACCC
  Q  M  G  I  D  D  S  S  K  D  N  R  G  A  Q  D  A  L  N  P>

1990       2000       2010       2020       2030       2040
          *          *          *          *          *          *
CGAGGATGAGGTCGATGAGTTCCTGGGCCGTGCCATCGATGCCCGCAGCATCGATCAGCT
  E  D  E  V  D  E  F  L  G  R  A  I  D  A  R  S  I  D  Q  L>

2050       2060       2070       2080       2090       2100
          *          *          *          *          *          *
ACGGAAGGACCATGTGCGCCGCTTCCTGCTCACCTTCCAGAGAGAGGATCTTGAAAAGAA
  R  K  D  H  V  R  R  F  L  L  T  F  Q  R  E  D  L  E  K  K>

2110       2120       2130       2140       2150       2160
          *          *          *          *          *          *
GTACTCAAGGAAGGTGGACCCCCGCTTCGGAGCCTACGTGGCCTGTGCGCTGTTGGTCTT
  Y  S  R  K  V  D  P  R  F  G  A  Y  V  A  C  A  L  L  V  F>

2170       2180       2190       2200       2210       2220
          *          *          *          *          *          *
CTGCTTCATCTGCTTTATCCAGCTCCTCGTCTTCCCACACTCAACCGTGATGCTTGGGAT
  C  F  I  C  F  I  Q  L  L  V  F  P  H  S  T  V  M  L  G  I>
```

FIG. 2D

```
      2230      2240      2250      2260      2270      2280
        *         *         *         *         *         *
    CTACGCCAGTATCTTTGTGCTGTTGCTGATCACCGTGCTGACCTGTGCCGTGTACTCCTG
     Y  A  S  I  F  V  L  L  L  I  T  V  L  T  C  A  V  Y  S  C>

2290      2300      2310      2320      2330      2340
        *         *         *         *         *         *
    TGGCTCTCTCTTCCCCAAGGCCCTGCGACGTCTTTCCCGCAGCATCGTCCGCTCTCGGGC
     G  S  L  F  P  K  A  L  R  R  L  S  R  S  I  V  R  S  R  A>

2350      2360      2370      2380      2390      2400
        *         *         *         *         *         *
    ACACAGCACTGTGGTTGGCATTTTTTCAGTCTTGCTAGTGTTCACCTCTGCCATCGCCAA
     H  S  T  V  V  G  I  F  S  V  L  L  V  F  T  S  A  I  A  N>

2410      2420      2430      2440      2450      2460
        *         *         *         *         *         *
    CATGTTCACCTGTAACCACACCCCCATCCGGACCTGTGCAGCCCGGATGCTGAATGTAAC
     M  F  T  C  N  H  T  P  I  R  T  C  A  A  R  M  L  N  V  T>

2470      2480      2490      2500      2510      2520
        *         *         *         *         *         *
    ACCCGCTGACATCACTGCCTGCCACCTGCAGCAGCTCAATTACTCTCTGGGCCTGGATGC
     P  A  D  I  T  A  C  H  L  Q  Q  L  N  Y  S  L  G  L  D  A>

2530      2540      2550      2560      2570      2580
        *         *         *         *         *         *
    TCCGCTGTGTGAGGGCACCGCACCCACTTGCAGCTTCCCTGAGTACTTCGTTGGGAACAT
     P  L  C  E  G  T  A  P  T  C  S  F  P  E  Y  F  V  G  N  M>

2590      2600      2610      2620      2630      2640
        *         *         *         *         *         *
    GCTGCTGAGTCTCTTGGCCAGCTCTGTTTTCCTGCACATCAGTAGCATCGGGAAGTTGGC
     L  L  S  L  L  A  S  S  V  F  L  H  I  S  S  I  G  K  L  A>

2650      2660      2670      2680      2690      2700
        *         *         *         *         *         *
    CATGATCTTTGTCCTGGGGCTCATTTATTTGGTGCTGCTTCTGCTGGGCCCCCCCAGCAC
     M  I  F  V  L  G  L  I  Y  L  V  L  L  L  G  P  P  S  T>

2710      2720      2730      2740      2750      2760
        *         *         *         *         *         *
    CATCTTTGACAACTATGACCTGCTGCTTGGTGTCCATGGCTTGGCTTCTTCCAATGACAC
     I  F  D  N  Y  D  L  L  L  G  V  H  G  L  A  S  S  N  D  T>
```

FIG. 2E

```
     2770      2780      2790      2800      2810      2820
       *         *         *         *         *         *
CTTTGATGGGCTGGACTGCCCAGCTGCGGGGAGGGTGGCACTGAAATACATGACCCCTGT
  F  D  G  L  D  C  P  A  A  G  R  V  A  L  K  Y  M  T  P  V>

2830      2840      2850      2860      2870      2880
       *         *         *         *         *         *
GATTCTGCTGGTGTTTGCCCTGGCGCTGTATCTGCACGCCCAGCAGGTGGAATCAACTGC
  I  L  L  V  F  A  L  A  L  Y  L  H  A  Q  Q  V  E  S  T  A>

2890      2900      2910      2920      2930      2940
       *         *         *         *         *         *
ACGTCTGGACTTCCTCTGGAAACTGCAGGCAACGGGGGAGAAGGAGGAGATGGAGGAGCT
  R  L  D  F  L  W  K  L  Q  A  T  G  E  K  E  E  M  E  E  L>

2950      2960      2970      2980      2990      3000
       *         *         *         *         *         *
CCAGGCCTACAACCGAAGGCTGCTGCATAACATTCTGCCTAAGGACGTGGCTGCCCACTT
  Q  A  Y  N  R  R  L  L  H  N  I  L  P  K  D  V  A  A  H  F>

3010      3020      3030      3040      3050      3060
       *         *         *         *         *         *
CCTGGCCCGGGAGCGCCGGAACGATGAGCTCTACTACCAGTCGTGTGAGTGTGTGGCCGT
  L  A  R  E  R  R  N  D  E  L  Y  Y  Q  S  C  E  C  V  A  V>

3070      3080      3090      3100      3110      3120
       *         *         *         *         *         *
CATGTTTGCCTCCATTGCCAACTTTTCTGAGTTCTATGTGGAGCTGGAGGCAAACAATGA
  M  F  A  S  I  A  N  F  S  E  F  Y  V  E  L  E  A  N  N  E>

3130      3140      3150      3160      3170      3180
       *         *         *         *         *         *
GGGTGTCGAGTGCCTGCGGCTGCTCAACGAAATCATCGCCGACTTTGATGAGATCATCAG
  G  V  E  C  L  R  L  L  N  E  I  I  A  D  F  D  E  I  I  S>

3190      3200      3210      3220      3230      3240
       *         *         *         *         *         *
CGAGGAGCGGTTCCGGCAGCTGGAGAAAATCAAGACGATCGGTAGCACGTACATGGCTGC
  E  E  R  F  R  Q  L  E  K  I  K  T  I  G  S  T  Y  M  A  A>

3250      3260      3270      3280      3290      3300
       *         *         *         *         *         *
GTCGGGGCTGAACGCCAGCACCTACGATCAGGCCGGCCGCTCCCACATCACTGCCCTGGC
  S  G  L  N  A  S  T  Y  D  Q  A  G  R  S  H  I  T  A  L  A>
```

FIG. 2F

```
            3310         3320         3330         3340         3350         3360
             *            *            *            *            *            *
      CGACTATGCCATGCGGCTCATGGAGCAGATGAAACACATCAACGAGCACTCCTTCAACAA
       D  Y  A  M  R  L  M  E  Q  M  K  H  I  N  E  H  S  F  N  N>

3370         3380         3390         3400         3410         3420
             *            *            *            *            *            *
      CTTCCAGATGAAGATTGGGCTGAACATGGGCCCAGTTGTGGCAGGCGTCATTGGGGCTCG
       F  Q  M  K  I  G  L  N  M  G  P  V  V  A  G  V  I  G  A  R>

3430         3440         3450         3460         3470         3480
             *            *            *            *            *            *
      GAAGCCACAGTATGACATCTGGGGGAACACGGTGAATGTCTCTAGCCGTATGGACAGCAC
       K  P  Q  Y  D  I  W  G  N  T  V  N  V  S  S  R  M  D  S  T>

3490         3500         3510         3520         3530         3540
             *            *            *            *            *            *
      GGGGGTTCCTGACCGAATCCAGGTGACCACGGACTTGTACCAGGTTCTAGCTGCCAAACG
       G  V  P  D  R  I  Q  V  T  T  D  L  Y  Q  V  L  A  A  K  R>

3550         3560         3570         3580         3590         3600
             *            *            *            *            *            *
      GTACCAGCTGGAGTGTCGAGGGGTGGTCAAGGTGAAGGGCAAGGGGGAGATGACCACCTA
       Y  Q  L  E  C  R  G  V  V  K  V  K  G  K  G  E  M  T  T  Y>

3610         3620         3630         3640         3650         3660
             *            *            *            *            *            *
      CTTCCTCAATGGGGCCCCCCCAGTTAGCAGACGCCAGCTACAAGTTCAGCTGTCAGGAC
       F  L  N  G  G  P  P  S 3670         3680         3690         3700         3710         3720
             *            *            *            *            *            *
      CAAGGTGGGCATTTAAGTGGACTCTGTGCTCGCTGGATGGAGCTGTGGCCGGGGGCACCA 3730         3740         3750         3760         3770         3780
             *            *            *            *            *            *
      AGCCTCCAGACCCTGCTGACCACAAAAGGGAACACCTCAGCAGGCTGTGCTTGGACCATG 3790         3800         3810         3820         3830         3840
             *            *            *            *            *            *
      CTCGTCTGCCCTCAGGCTGGTGAACAAGGGATACCAAGAGGATTATGCAAGTGACTTTTA 3850         3860         3870         3880         3890         3900
             *            *            *            *            *            *
      CTTTTCTAATTGGGGTAGGGCTGGCTGTTCCCTCTTTCTTCCTGCTTTTGGGAGCAGGGG
```

FIG. 2G

```
           3910        3920        3930        3940        3950        3960
             *           *           *           *           *           *
       AGGCAGCTGCAGCAGAGGCAGCAGGAGCCCTCCTGCCTGAGGGTTTAAAATGGCAGCTTG 3970        3980        3990        4000        4010        4020
             *           *           *           *           *           *
       CCATGCCTACCCTTTCCCCTGTCTGTCTGGGCAACAGCATCGGGGCTGGGCCCTTCCTTT 4030        4040
             *           *
       CCCTCTTTTTCCTGGGAATATTTTGT
```

FIG. 2H

CLONING AND CHARACTERIZATION OF A CARDIAC ADENYLYL CYCLASE

FIELD OF THE INVENTION

This invention relates to a DNA sequence encoding a novel effector enzyme referred to as a cardiac adenylyl cyclase. This invention also relates to the amino acid sequence of the cardiac adenylyl cyclase encoded by that DNA sequence.

BACKGROUND OF THE INVENTION

The signal transduction pathway may be subdivided into three steps. The first is the recognition of the ligand by the receptor. The second is the transmission and amplification of the signal by a "transducer" protein. The final step is the generation of the second messenger by an effector enzyme.

Adenylyl cyclases are effector enzymes that are coupled to various hormone-receptor systems, such as catecholamine and ACTH. The catecholamine receptor and its transducer protein (G-protein) have been well characterized since the cloning of their cDNAs. However, relatively little is known about the adenylyl cyclase.

Once such a hormone binds to the receptor, it activates G protein, a heterotrimeric guanine nucleotide-binding regulatory protein ($\alpha$, $\beta$, $\gamma$). The activated G-protein elicits the exchange of GDP for GTP, as well as the dissociation from $\beta\gamma$ subunits. The GTP bound form of the $\alpha$-subunit stimulates adenylyl cyclase, which generates cyclic AMP from ATP. Cyclic AMP, a second messenger, activates various proteins, including protein kinases.

Protein kinases then phosphorylate other proteins, thus initiating a signal transduction cascade. Another type of activation is through the increased intracellular calcium concentration, especially in nervous tissues. After depolarization, the influx of calcium elicits the activation of calmodulin, an intracellular calcium binding protein. The activated calmodulin has been shown to bind and activate an adenylyl cyclase directly (Bibliography 1).

Several papers have suggested the diversity of the adenylyl cyclases. Using forskolin-bound affinity chromatography, a single class of the enzyme protein was purified from bovine brain (2,3). The monoclonal antibody raised against this purified protein also recognized another form of protein in the brain, which was different in size. Biochemical characteristics have shown that these two are different types of adenylyl cyclase; one is calmoduline-sensitive (CaM-sensitive) and the other is CaM-insensitive. This study (2) showed that there are two types of adenylyl cyclase in one tissue, and that these types share the same domain that could be recognized by the same antibody.

Another paper has presented genetic evidence of the diversity of adenylyl cyclase (4). An X-linked recessive mutation in Drosophilla which blocked associative learning lacked the CaM-sensitivity of adenylyl cyclase, but did possess the reactivity to fluoride or GTP. This suggests that the CaM-sensitive cyclase gene is located in the X-chromosome, which is distinct from the CaM-insensitive adenylyl cyclase gene.

Three different cDNAs have been cloned from mammalian tissues so far. These have been designated type I (brain type (5)); II (lung type (6)); and III (olfactory type (7)). The cDNA sequences of Types I and III have been published. The adenylyl cyclases coded for by these cDNAs are large proteins more than 1000 amino acids in length. Topographically, all types are similar. All have two six-transmembrane domains associated with a large cytoplasmic loop. The amino acid sequence of the cytoplasmic loop is conserved among different types of cyclase.

Tissue distribution of these adenylyl cyclase messages is well distinguished, as shown in Northern blotting studies. Type I is expressed only in the brain, type II is distributed in lung and brain, and type III is expressed mostly in the olfactory tissue with little expression in the brain. Thus, the adenylyl cyclases are distributed in a rather tissue specific manner. Despite the fact that heart tissue was one of the tissues in which adenylyl cyclase was originally identified, none of the three known types has been shown to be expressed in heart tissue.

It has been documented that a form of adenylyl cyclase is also present in the heart (8), and that the cyclase from the heart is recognized by a monoclonal antibody originally raised against the cyclase from the brain (9). Given that the three cloned types of adenylyl cyclase have a conserved amino acid sequence in their large cytoplasmic loop, the cyclase from the heart may share sequence homology in this region. Thus, it is possible to attempt to obtain an adenylyl cyclase clone from the heart by using an adenylyl cyclase cDNA from the brain. However, no adenylyl cyclase has been reported to have been cloned from cardiac tissue or expressed.

SUMMARY OF THE INVENTION

The starting point of this invention is the hypothesis that any adenylyl cyclase in the heart should share significant homology with that from the brain, and that it could be screened using a probe from the cyclase of the brain. The adenylyl cyclase in the heart has been shown to be related with the development of heart failure (10). This suggests it is involved with cardiac function.

According to this invention, a novel type of adenylyl cyclase cDNA is cloned from a canine heart library. This novel adenylyl cyclase is referred to as cardiac adenylyl cyclase (B form). This cardiac adenylyl cyclase is composed of 1165 amino acids. Another form (A form) of cardiac adenylyl cyclase, composed of 1019 amino acids, is the subject of co-pending, commonly-assigned application Ser. No. 07/751,460, filed Aug. 29, 1991.

This B form of cardiac adenylyl cyclase is expressed predominantly in the heart, as well as in the brain, but to a lesser degree in other tissues.

The B form of cyclase is translated from the cDNA in a transient expression system using CMT cells. CMT is a monkey kidney cell line stably transformed with a T-antigen gene driven by the metallothionein promoter. This cyclase is stimulated by forskolin, which is known to stimulate adenylyl cyclase activity in the heart (10).

The structure of this B form of cardiac adenylyl cyclase is similar to those of other types of adenylyl cyclase. It contains the motif of 6-transmembrane spanning regions associated with a large cytoplasmic loop. The overall homology of the amino acid sequences of the A and B forms of cardiac adenylyl cyclases is 64%. Their amino acid sequences are more homologous in the cytoplasmic portions than in the transmembrane portions. The B form of cardiac adenylyl cyclase may be involved in the regulation of cardiac function. Unless otherwise stated, the balance of this application is directed to the B form of cyclase; the A form is described in the co-pending application referred to above.

Panel A depicts a partial restriction map of adenylyl cyclase cDNA. The coding portion is boxed and a hatched box shows the polyadenylation site. N stands for NarI restriction site, S for SphI, SS for SspI and P for PstI; ATG, a translation initiation codon, and TAG, a translation termination codon are shown.

Panel B depicts two cDNA clones, numbered 6 and 27, obtained from the canine heart λgt 10 library.

FIGS. 2a–2h depict the DNA and predicted amino acid sequence of the cardiac adenylyl cyclase. The entire coding sequence, as well as portions of the 5' and 3' untranslated sequences, are shown. The whole sequence is done bidirectionally twice by dideoxy sequencing method using either Sequanase or Taq polymerase. An arrow shows the possible translation initiation site (ATG) in an open reading frame. This ATG is accompanied by the most conserved Kozak consensus sequence.

Figure 3:
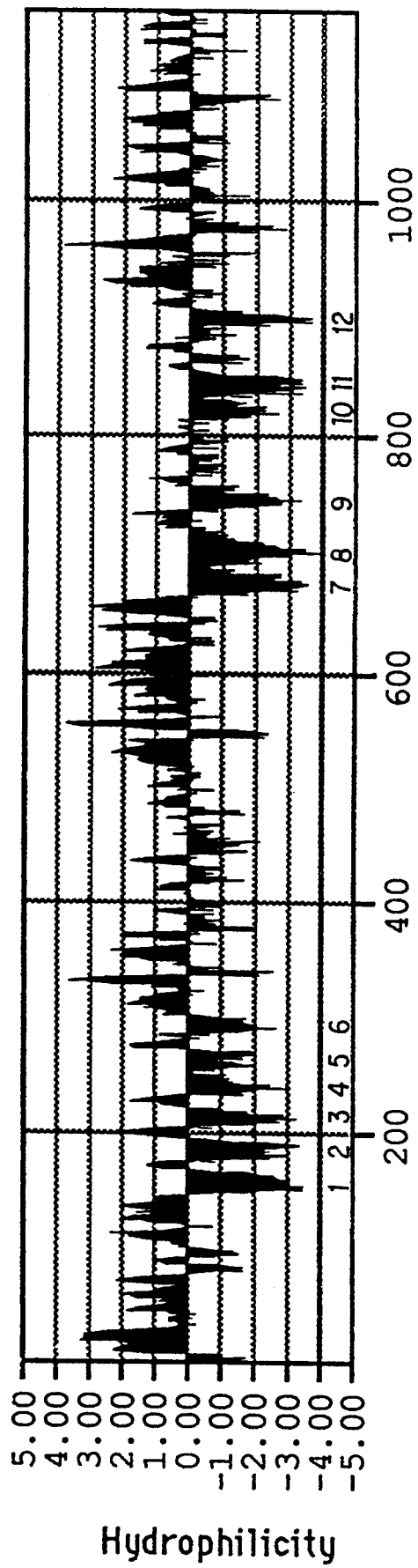

FIG. 3 depicts a hydropathy plot of the cardiac adenylyl cyclase. MacVector 3.5 software is used to analyze the membrane related structure of cardiac adenylyl cyclase. The method of Kyte and Doolittle (11) is used with a window size of 7.

Figure 4:
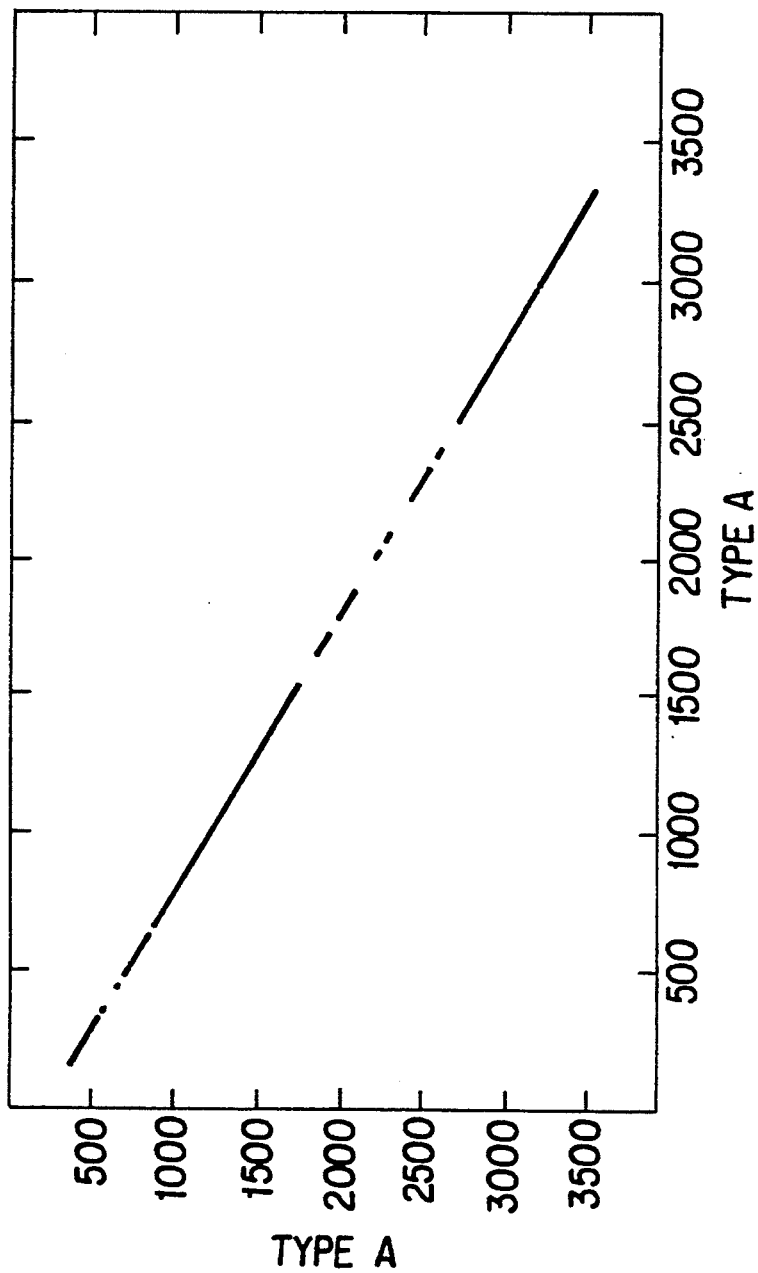

FIG. 4 depicts a DNA dot matrix comparison between the A and B forms of cardiac adenylyl cyclase. MacVector 3.0 software is used for the analysis with a stringency of 65% and a window size of 8.

Figure 5:
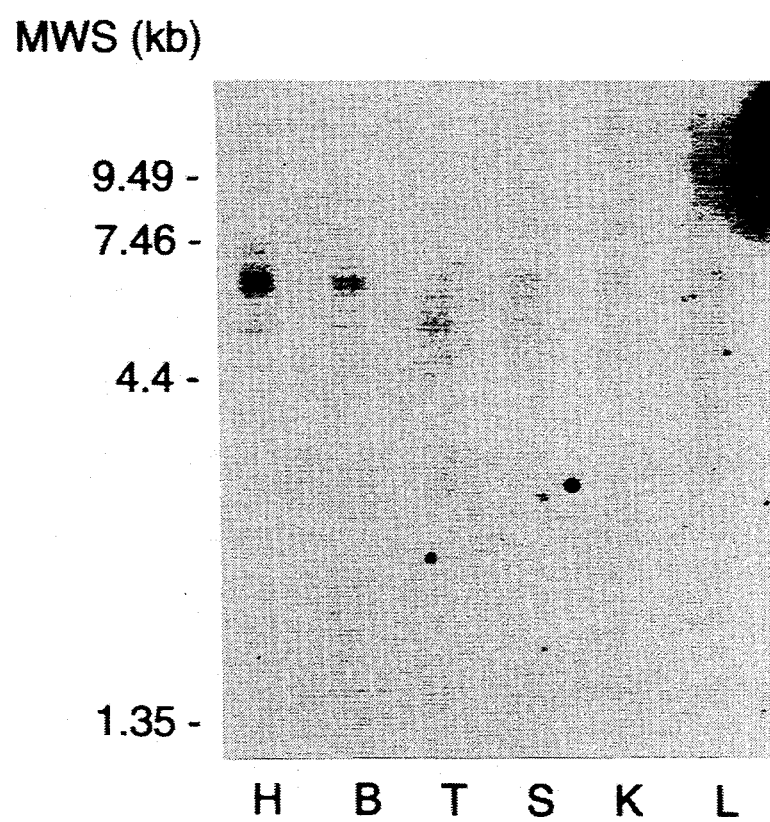

FIG. 5 depicts Northern blot analysis of various canine tissues by a fragment from cardiac adenylyl cyclase cDNA. The lanes are as follows: H-heart, B-brain, T-testis, S-skeletal muscle, K-kidney, L-lung. Standards in kilobases (kb) are at the left of the blot.

DETAILED DESCRIPTION OF THE INVENTION

The strategy used to identify and isolate the novel cardiac adenylyl cyclase begins with the construction and screening of canine heart cDNA library.

Left ventricular tissue of canine heart is used as a source of mRNA. The library is prepared in a λgt10 phage with an oligo-dT primer as described (12). The primary screening of the λgt10 library is carried out with gentle washing (less stringent conditions). Approximately $2 \times 10^6$ plaques are initially screened from the library. Prehybridization is carried out for at least two hours in a solution containing 30% formamide, $5 \times SSC$, $5 \times$ Denhardt's, 25 mM NaPO$_4$ (pH 6.5), 0.25 mg/ml calf thymus DNA, and 0.1% sodium dodecyl sulfate (SDS) at 42° C. Hybridization is then performed in the same solution at 42° C. An 970 base pair (bp) AatI-HincII fragment from type I adenylyl cyclase cDNA is used as a probe. This fragment encodes the first cytoplasmic domain of the adenylyl cyclase, which has significant homology to other previously-known types of adenylyl cyclase (7).

The probe is radiolabelled with $^{32}$P-dCTP by the multi-primer-random labelling method. After hybridization for 18 hours, the blot is washed under increasingly stringent conditions and then radioautographed. One positive clone is obtained. The size of the insert in the clone is 5.4 kb (kilobases).

The next step is to ascertain the full length cDNA sequence from the inserts in the clones. All the positive clones from the canine heart library are subcloned into plasmid pUC18. After restriction maps are made, they are further subcloned and sequenced with universal primers or synthesized oligomers. For some fragments, sequencing is performed after a series of deletions is made by exonuclease III digestion. The sequence is performed bidirectionally at least twice with either Sequenase (13) or by Taq polymerase (14). In some GC-rich areas, the sequence is performed using a gel containing 7% polyacrylamide, 8 M urea, and 20% formamide.

Figure 1:
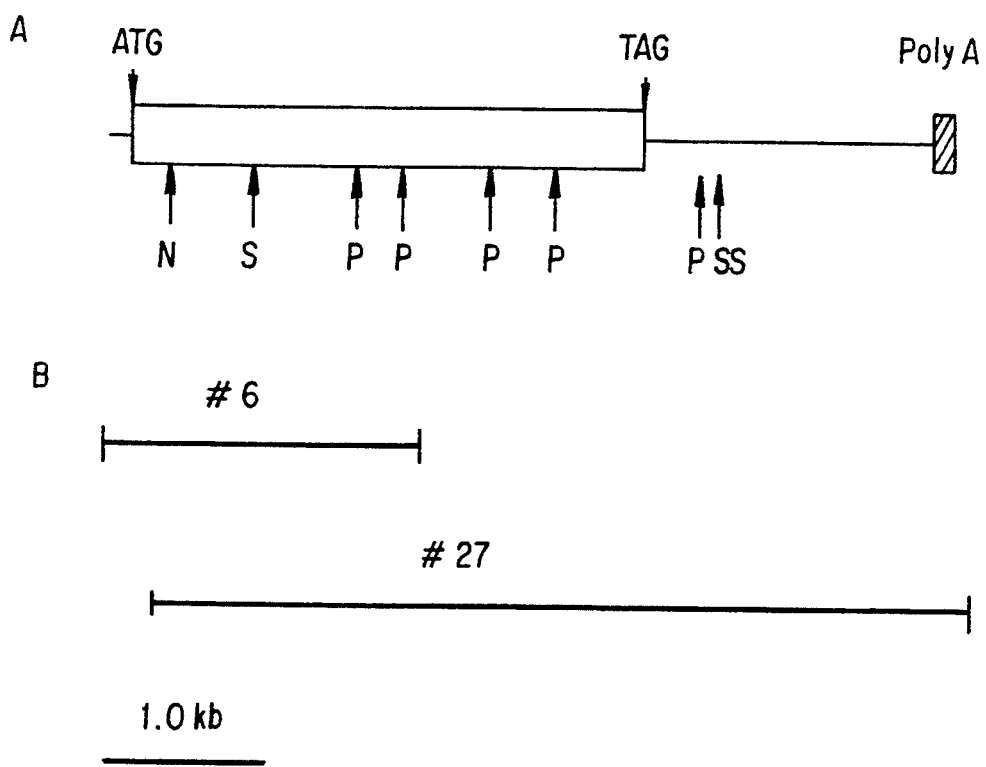
FIG. 1 depicts a partial restriction map and the cDNA clone of the cardiac adenylyl cyclase (B form).

A clone designated #27 is found to be of particular interest. After the entire coding portion of clone #27 is sequenced, it is found that it contains an insert of 5.4 kb with a polyadenylation signal at its 3' end (FIG. 1). However, it does not contain an ATG with a conserved Kozak consensus sequence, which provides a favorable context for initiating translation (15).

A 5' EcoRI-SphI fragment from clone #27 is therefore used as a probe to rescreen the library. Several clones are obtained. It is found that a clone designated #6 overlaps for 800 bases with clone #27, and extends the cDNA sequence upstream an additional 441 bp. After sequencing the whole insert, an ATG with conserved Kozak consensus sequence is found at its 5' end (arrow, FIG. 1). This open reading frame of 3495 bases reads through to a TAG, a translation termination codon (FIGS. 1 and 2). Thus, clones #27 and #6 encode a protein of 1165 amino acids, which is 147 amino acids longer than the A form of cardiac adenylyl cyclase. The entire coding portion of the cDNA and its predicted amino acid sequence are shown (FIG. 2) (SEQ ID NO: 1).

A 4.0 kb EcoRI-SspI fragment from clones #6 (EcoRI-SphI) and #27 (SphI-SspI) is subcloned into pcDNAamp (formed by introducing an ampicillin resistance gene into pcDNA1, obtained from Invitrogen). The resulting expression vector, containing the full length cDNA, is designated pcDNAamp/27-6. Samples of this expression vector, inserted into an appropriate *E. coli* strain designated DH5alpha, have been deposited with the American Type Culture Collection, 12301 Parklawn Drive, Rockville, Md. 20852, in accordance with the Budapest Treaty on the International Recognition of the Deposit of Microorganisms for the Purposes of Patent Procedure and have been accorded accession number ATCC 68826.

Production of this cardiac adenylyl cyclase is achieved by the cloning and expression of the cardiac adenylyl cyclase cDNA in a suitable expression system using established recombinant DNA methods. Production of the cardiac adenylyl cyclase can be achieved by incorporation of the cardiac adenylyl cyclase cDNA into any suitable expression vector and subsequent transformation of an appropriate host cell with the vector; alternatively, the transformation of the host cell can be achieved directly by naked DNA without the use of a vector. Production of the cardiac adenylyl cyclase by either eukaryotic cells or prokaryotic cells is contemplated by the present invention. Examples of suitable eukaryotic cells include mammalian cells, plant cells, yeast cells and insect cells. Similarly, suitable prokaryotic hosts, in addition to *E. Coli*, include *Bacillus subtilis*.

Other suitable expression vectors may also be employed and are selected based upon the choice of host cell. For example, numerous vectors suitable for use in transforming bacterial cells are well known. For example, plasmids and bacteriophages, such as λ phage, are the most commonly used vectors for bacterial hosts, and for *E. coli* in particular. In both mammalian and insect cells, virus vectors are frequently used to obtain expression of exogenous DNA. In particular, mammalian cells are commonly transformed with SV40 or polyoma virus; and insect cells in culture may be transformed with baculovirus expression vectors. Yeast vector systems include yeast centromere plasmids, yeast episomal plasmids and yeast integrating plasmids.

It will also be understood that the practice of the invention is not limited to the use of the exact sequence of the cardiac adenylyl cyclase cDNA as defined in FIG. 2 (SEQ ID NO: 1). Modifications to the sequence, such as deletions, insertions, or substitutions in the sequence which produce silent changes in the resulting protein molecule are also contemplated. For example, alterations in the cDNA sequence which result in the production of a chemically equivalent amino acid at a given site are contemplated; thus, a codon for the amino acid alanine, a hydrophobic amino acid, can readily be substituted by a codon encoding another hydrophobic residue, such as glycine, or may be substituted with a more hydrophobic residue such as valine, leucine, or isoleucine. Similarly, changes which result in substitution of one negatively charged residue for another, such as aspattic acid for glutamic acid, or one positively charged residue for another, such as lysine for arginine, can also be expected to produce a biologically equivalent product.

Nucleotide changes which result in alteration of the N-terminal and C-terminal portions of the protein molecule frequently do not alter protein activity, as these regions are usually not involved in biological activity. It may also be desirable to eliminate one or more of the cysteines present in the sequence, as the presence of cysteines may result in the undesirable formation of multimers when the protein is produced recombinantly, thereby complicating the purification and crystallization processes.

Each of the proposed modifications is well within the routine skill in the art, as is determination or retention of biological activity of the encoded products. Therefore, where the phrase "cardiac adenylyl cyclase cDNA sequence" or "cardiac adenylyl cyclase gene" is used in either the specification or the claims, it will be understood to encompass all such modifications and variations which result in the production of a biologically equivalent cardiac adenylyl cyclase protein. It is also understood to include the corresponding sequence in other mammalian species. In particular, the invention contemplates those DNA sequences which are sufficiently duplicative of the sequence of FIG. 2 so as to permit hybridization therewith under standard high stringency Southern hybridization conditions, such a those described in Maniatis et al. (16).

In an example of such expression, twenty μg of the purified plasmid pcDNAamp/27-6 are transfected into the monkey kidney CMT cells using a modified method of Goolub et al. (17). Briefly, the cells are grown to 80% confluence in Dulbecco's modification of Eagle's Medium, 10% fetal calf serum, 2 mM glutamine, 4.5 mg/ml glucose, 10 μg/ml streptomycin sulfate and 60 μg/ml penicillin K. After washing with PBS twice, 0.5 ml of trypsin solution is added. The cells are incubated for 10 minutes, and 20 μg of purified plasmid resuspended in 4 ml of DMEM containing 400 μg/ml DEAE dextran and 0.1 mM chloroquine is added. The cell is incubated for four hours followed by 10% DMSO shock for two minutes. After washing with PBS twice, the induction media, which contains 10% fetal calf serum (FCS), 2 mM glutamine, 4.5 g/ml glucose, 2 mM penicillin and streptomycin, and 1 μM $CdCl_2$, 0.1 μM $ZnCl_2$ in DMEM, is added. The plate is incubated at 37° C. for 72 hours before harvesting.

This adenylyl cyclase protein, composed of 1165 amino acids, is analyzed for secondary structure by the method of Kyte-Doolittle (11) (FIG. 3). The software, MacVector 3.5 (IBI, New Haven, CT), is used to obtain a hydropathy plot and thereby identify the membrane related structure of this cardiac adenylyl cyclase. The method of Kyte and Doolittle is used with a window size of 7.

As shown in FIG. 3, twelve peaks are numbered. These peaks represent transmembrane spanning regions. These results suggest that this cardiac adenylyl cyclase possesses a structure of twelve transmembrane spanning regions, as well as a large cytoplasmic loop located in the middle and at the end. In the transmembrane positions, the fifth extracellular loop is the largest (between the ninth and tenth transmembrane spans).

One hundred and fifty amino acids of the N-terminal tail are located in the cytoplasm, followed by a 6-transmembrane spanning region of 154 amino acids (amino acid position 151–304). Then 363 amino acids of the cytoplasmic domains (305–667) precede the second 6-transmembrane spanning domain of 242 amino acids (668–909), followed by another cytoplasmic domain of 256 amino acids (910–1165). Thus it makes a duplicated form of 6-transmembrane spanning region and large hydrophobic cytoplasmic domain.

As shown in FIG. 4, a DNA dot matrix comparison between the B form and the A form of cardiac adenylyl cyclase, the two large hydrophobic cytoplasmic loops show homology of 72–80% with each other. The homology between the two transmembrane spanning portions is also high (44–45%).

Thus, these two cardiac cyclases are clearly distinct from each other, but share much higher homology than with other types of cyclases, such as type I and type III. It is therefore reasonable to categorize these cardiac adenylyl cyclases as a new subclass of the entire adenylyl cyclase family. The only distinct difference between the two cardiac cyclases is that the A form lacks an N-terminal cytoplasmic domain, while the B form possesses such a domain 150 amino acids in length.

The membrane associated secondary structure of the protein (based on the results of FIG. 3) is well conserved among different types of mammalian adenylyl cyclases (types I, II, III, and cardiac types). All of them possess two large cytoplasmic loops, interrupted by the presence of 6-transmembrane spanning region. The homology among the different types of adenylyl cyclase is only conserved in the cytoplasmic portions, even though the other portions are structurally similar. Furthermore, in the same adenylyl cyclase protein the homology between the two cytoplasmic portions is also maintained. This suggests the cytoplasmic portion is a result of gene duplication.

It has been suggested that the level of activity of the adenylyl cyclases in the heart correlates with the development of heart failure. There is a significant decrease in the cyclase activity in the failed heart compared with that in the non-failed heart (10,18,19,20). These papers suggest that there is a distal regulation in the signal transduction pathway, i.e., the regulation at the level of cyclase. In fact, the decreased activity of adenylyl cyclase in the heart may be the major factor in the development of heart failure. Thus, the novel cardiac adenylyl cyclase of this invention is used to screen for compounds which stimulate the activity of that cyclase.

The biochemical property of this cardiac adenylyl cyclase is examined in a transient expression system using CMT cells (a derivative of COS cells). CMT cells contain T-antigen driven by a methalothionein promoter in the genome. Thus by induction with heavy metal ion in the medium, CMT cells could produce more T-antigen than COS cells. A 4.0 kb fragment of the adenylyl cyclase cDNA containing the whole coding sequence is inserted into the pcDNAamp plasmid described above.

The adenylyl cyclase activity of a membrane transfected with the expression vector pcDNAamp carrying cardiac adenylyl cyclase cDNA is assayed as follows. The transfected CMT cells are washed twice with PBS and scraped in three ml of cold buffer containing 50 mM Tris (pH 8.0), 1 mM EDTA, 10 $\mu$M PMSF (pheynlmethylsulfonylfluoride), 100 U leupeptin, and 50 U egg white trypsin inhibitor (ETI) on ice. The membrane is homogenated in Polytron TM (setting 6 for 10 seconds) and is centrifuged at 800$\times$g for 10 minutes at 4° C. The supernatant is further centrifuged at 100$\times$g for 40 minutes at 4° C. The resultant pellet is resuspended in 50 mM Tris (pH 8.0), 1 mM EDTA, 1 $\mu$M PMSF, 50 U leupeptin, and 50 U ETI, to a concentration of 5 $\mu$g/$\mu$l. This crude membrane solution is used for the adenylyl cyclase asssay.

The adenylyl cyclase assay is performed by the method of Salomon (21). Briefly, the crude membranes from CMT cells are resuspended in a solution containing 1 mM creatine phosphate, 8 $\mu$g/ml creatine phophokinase, 4 mM HEPES (pH 8.0), 2 mM MgC12, 0.1 mM c-AMP 0.1 mM ATP, and $^{32}$P-ATP (0 2-5 $\mu$Ci/assay tube). The reaction mixture is incubated at 37° C. for 30 minutes and the reaction is stopped by the addition of 100 $\mu$l % sodium dauryl sulfate. To monitor the recovery from the column, $^3$H-labelled c-AMP is used. Cyclic-AMP is separated from ATP by passing through Dowex and alumina columns, and the radioactivity is counted by scintillation counter. The protein concentrations of the membranes used are measured by Bradford's method (22), with bovine serum albumin as a standard.

The membrane from untransfected CMT cells is used as a control. The results of the adenylyl cyclase activity assay are shown in Table 1:

TABLE 1

|  | Basal* | NaF* | GTP$\gamma$S* | Forskolin* |
| --- | --- | --- | --- | --- |
| Control | 4 $\pm$ 0.7 | 17 $\pm$ 3 | 30 $\pm$ 5 | 61 $\pm$ 11 |
| Transfected | 9 $\pm$ 1 | 46 $\pm$ 5 | 114 $\pm$ 12 | 223 $\pm$ 27 |

*control < transfected, p < 0.05, control (n = 6), transfected (n = 8)

The adenylyl cyclase expressed by this cDNA is well stimulated by 10 mM sodium fluoride, 100 $\mu$M GTP$\gamma$S and 100 $\mu$M forskolin. It shows 2.7, 3.8 and 3.7 fold more stimulation than the control. Values are shown with $\pm$ standard error.

An increased basal activity of adenylyl cyclase in the transfected cells is also observed. This suggests that this cyclase possesses high basal activity, allowing high accumulation of cyclic AMP in the heart. This is consistent with the high basal cyclase activity seen in cardiac tissue.

In order to clarify the tissue distribution of the cardiac adenylyl cyclase (B form), Northern blotting is performed using mRNA from various tissues. Messenger RNA is purified using guanidium sodium (20) and oligo-dT columns from various canine tissues (heart, brain, testis, skeletal muscle, kidney and lung). Five $\mu$g of mRNA are used for each assay (per lane of blot).

The blot is prehybridized in a solution containing 50% formamide, 5$\times$SSC, 5$\times$Denhardt's, 25 mM NaPO$_4$ (pH 6.5), 0.25 mg/ml calf thymus DNA, and 0.1% SDS at 42° C. for two hours before the addition of a probe. The entire 5.4 kb CDNA fragment from the adenyly cyclase cDNA clone #27 is used as a probe. The probe is made by a multiprimer random labelling method with $^{32}$P-dCTP. Hybridization is performed at 42° C. for 18 hours followed by washing under increasingly stringent conditions. The blot is then autoradiographed.

The results of the Northern blot analysis, as depicted in FIG. 5, show that the message is most abundant in the heart, as well as in the brain, but much less expressed in other tissues, such as testis, skeletal muscle, kidney and lung.

The single class of message which hybridizes with a fragment from clone #27 is 6 kb in size, clearly distinct from the messages (5 and 7 kb) with clone #113 which contains the cDNA for the A form of the cyclase.

BIBLIOGRAPHY

1. Salter, R. S., et al., *J. Biol. Chem.*, 256, 9830-9833 (1981).
2. Pfeuffer E., et al., *EMBO J.*, 4, 675-3679 (1985).
3. Mollnet, S., et al., *Eur. J. Biochem.*, 195, 281-286 (1991).
4. Livingstone, M. S., et al., *Cell*, 37, 205-215 (1984).
5. Krupinski, J., et al., *Science*, 244, 558-1564 (1989).
6. Tang, W. T., et al., *J. Biol. Chem.*, 266, 595-8603 (1991).
7. Bakalyar, H. A., and Reed, R. R., *Science*, 250, 1403-1406 (1990).
8. Pfeuffer, E., et al., *Proc. Natl. Acad. Sci. USA.*, 82, 3086-3090 (m985).
9. Mollner, S., and Pfeuffer, T., *Eur. J. Biochem.*, 171, 265-271 (1988).
10. Chen, L., et al., J. Clin. Invest., 87, 293-298 (1991).
11. Kyte, J., and Doolittle, R. F., *J. Mol. Biol.*, 157, 105-132 (1982).
12. Watson, C. J. and Jackson, J. F., in *DNA Cloning: A Practical Approach*, Glover, D. M., ed., vol. 1, pp.79-88 (1985).
13. Tabor, S., and Richardson, C. C., *Proc. Natl. Acad, Sci., USA*, 84, 4767-4771 (1987).
14. Innis, M. A., et al., *Proc. Natl. Acad. Sci. USA*, 85, 9436-9440 (1988).
15. Kozak, M., *J. Cell. Biol.*, 108, 229-241 (1989).
16. Maniatis et al., *Molecular Cloning: A Laboratory Manual*, Cold Spring Harbor Laboratory, (1982).
17. Goolub, E. I., et al., *Nucleic Acid Research*, 17, 4902 (1989).
18. Robberecht, P., et al., *Biochem. Pharmacol.*, 30, 385-387 (1981).
19. Chatelain, P., et al., *Eur. J. Pharmacol.*, 72, 17-25 (1981).
20. Palmer, G. C., and Greenberg, S., *Pharmacology*, 19, 156-162 (1979).

21. Salomon, Y., *Adv. Cyclic Nucleotide Res.*, 10, 35–55 (1979).

22. Bradford, M., *Anal. Biochem.*, 73, 248 (1976).

23. Chomczynski, P., and Sacchi, N., *Anal. Biochem.*, 162, 156–159 (1987).

---

What is claimed is:

1. A purified and isolated gene which has as the entire coding portion of its nucleotide sequence the sequence depicted in FIG. 2 and identified as SEQ ID NO: 1, which encodes a biologically active cardiac adenylyl cyclase.

2. A method for the production of a cardiac adenylyl cyclase which comprises incorporating the gene of claim 1 into an expression vector, transforming a host cell with said vector and culturing the transformed host cell under conditions which results in expression of the gene.

3. The method of claim 2 wherein the host cell comprises a bacterial, viral, yeast, insect or mammalian cell line.

4. A method of claim 3 wherein the expression vector is pcDNAamp/27-6.

5. An expression vector which includes the gene of claim 1.

6. The expression vector of claim 5, wherein said vector transfers a host cell comprising a bacterial, viral, yeast or mammalian cell line.

7. The expression vector of claim 6 which is a plasmid.

8. The expression vector of claim 7 which is pcDNAamp/27-6.

9. A host cell transformed with an expression vector which incorporates the gene of claim 1 (ATCC 68826).

10. The cell of claim 9 which is an *E. coli* DH5alpha strain transformed with pcDNAamp/27-6.

* * * * *

UNITED STATES PATENT AND TRADEMARK OFFICE
CERTIFICATE OF CORRECTION

PATENT NO. : 5,334,521
DATED : August 2, 1994
INVENTOR(S) : Yoshihiro Ishikawa It is certified that error appears in the above-identified patent and that said Letters Patent is hereby corrected as shown below:

```
Column 20:
    Claim 4, line 1, "A" should read --The--.

Claim 6, line 2, "transfers" should read
--transforms--.
```

Signed and Sealed this

Fourteenth Day of February, 1995

Attest:

BRUCE LEHMAN

Attesting Officer

Commissioner of Patents and Trademarks

UNITED STATES PATENT AND TRADEMARK OFFICE
CERTIFICATE OF CORRECTION

PATENT NO. : 5,334,521

DATED : August 2, 1994

INVENTOR(S) : Yoshihiro Ishikawa

It is certified that error appears in the above-indentified patent and that said Letters Patent is hereby corrected as shown below:

Delete Drawing Sheet 11 of 12, Figure 4, and substitute therefor the drawing sheet, consisting of Figure 4, as shown on the attached page.

UNITED STATES PATENT AND TRADEMARK OFFICE
CERTIFICATE OF CORRECTION

PATENT NO. : 5,334,521
DATED : August 2, 1994
INVENTOR(S) : Yoshihiro Ishikawa

It is certified that error appears in the above-indentified patent and that said Letters Patent is hereby corrected as shown below:

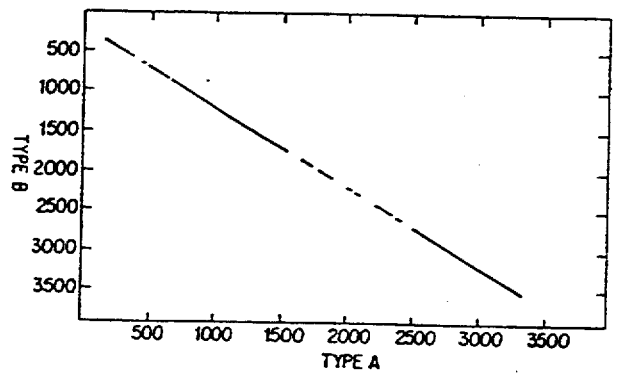

FIG. 4

Signed and Sealed this

Thirteenth Day of June, 1995

Attest:

BRUCE LEHMAN

Attesting Officer      Commissioner of Patents and Trademarks

UNITED STATES PATENT AND TRADEMARK OFFICE
CERTIFICATE OF CORRECTION

PATENT NO. : 5,334,521

DATED : August 2, 1994

INVENTOR(S) : YOSHIHIRO ISHIKAWA

It is certified that error appears in the above-identified patent and that said Letters Patent is hereby corrected as shown below:

Column 7, line 32, "asssay" should read --assay--.

Signed and Sealed this

Twelfth Day of September, 1995

Attest:

BRUCE LEHMAN

Attesting Officer  Commissioner of Patents and Trademarks

SEQUENCE LISTING (1) GENERAL INFORMATION:

(iii) NUMBER OF SEQUENCES: 1

(2) INFORMATION FOR SEQ ID NO: 1:

(i) SEQUENCE CHARACTERISTICS:
        (A) LENGTH: 4046 base pairs listed
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 1:

```
CGGCCGGGCG  GGCTGCGGGC  GGCGAGGCTC  GCCGGGGCGC                  40

GGGCGGCGGG  GGGCGCGGGG  CGGCCGGCCG  GGCCGGAGCC                  80

CGGGGGGCGG  CGGGGCGGGG  TCCGGGGCGG    CGCGGAGCGG               120

GGCCGGCAGC                                                     130

ATG  TCG  TGG  TTT  AGT  GGC  CTC  CTG  GTC  CCC  AAA  GTG     166
Met  Ser  Trp  Phe  Ser  Gly  Leu  Leu  Val  Pro  Lys  Val
 1                    5                        10

GAT  GAA  CGG  AAG  ACA  GCC  TGG  GGT  GAA  CGC  AAT  GGG     202
Asp  Glu  Arg  Lys  Thr  Ala  Trp  Gly  Glu  Arg  Asn  Gly
          15                        20

CAG  AAG  CGT  CCA  CGC  CGC  GGG  ACT  CGG  ACC  AGT  GGC     238
Gln  Lys  Arg  Pro  Arg  Arg  Gly  Thr  Arg  Thr  Ser  Gly
 25                        30                        35

TTC  TGC  ACG  CCC  CGC  TAT  ATG  AGC  TGC  CTC  CGG  GAT     274
Phe  Cys  Thr  Pro  Arg  Tyr  Met  Ser  Cys  Leu  Arg  Asp
               40                        45

GCG  CAG  CCC  CCC  AGT  CCC  ACC  CCT  GCG  GCT  CCC  CCT     310
Ala  Gln  Pro  Pro  Ser  Pro  Thr  Pro  Ala  Ala  Pro  Pro
      50                        55                        60

CGG  TGC  CCC  TGG  CAG  GAT  GAG  GCC  TTC  ATC  CGG  AGA     346
Arg  Cys  Pro  Trp  Gln  Asp  Glu  Ala  Phe  Ile  Arg  Arg
                    65                        70

GGC  GGC  CCG  GGC  AAG  GGC  ACG  GAG  CTG  GGG  CTG  CGG     382
Gly  Gly  Pro  Gly  Lys  Gly  Thr  Glu  Leu  Gly  Leu  Arg
               75                        80

GCG  GTG  GCC  CTG  GGC  TTC  GAG  GAC  ACT  GAG  GCC  ATG     418
Ala  Val  Ala  Leu  Gly  Phe  Glu  Asp  Thr  Glu  Ala  Met
 85                        90                        95

TCA  GCG  GTT  GGG  GCA  GCT  GGA  GGT  GGC  CCT  GAC  GTG     454
Ser  Ala  Val  Gly  Ala  Ala  Gly  Gly  Gly  Pro  Asp  Val
                   100                       105

ACC  CCC  GGG  AGT  AGG  CGA  TCC  TGC  TGG  CGC  CGT  CTG     490
Thr  Pro  Gly  Ser  Arg  Arg  Ser  Cys  Trp  Arg  Arg  Leu
     110                       115                       120

GCC  CAG  GTG  TTC  CAG  TCG  AAG  CAG  TTC  CGC  TCG  GCC     526
Ala  Gln  Val  Phe  Gln  Ser  Lys  Gln  Phe  Arg  Ser  Ala
                   125                       130

AAG  CTG  GAG  CGC  CTG  TAC  CAG  CGG  TAC  TTC  TTT  CAG     562
Lys  Leu  Glu  Arg  Leu  Tyr  Gln  Arg  Tyr  Phe  Phe  Gln
               135                       140

ATG  AAC  CAG  AGC  AGC  CTG  ACG  CTG  CTG  ATG  GCG  GTG     598
Met  Asn  Gln  Ser  Ser  Leu  Thr  Leu  Leu  Met  Ala  Val
145                       150                       155
```

| | | | | | | | | | | | |
|---|---|---|---|---|---|---|---|---|---|---|---|
| CTG | GTG | CTG | CTG | ACA | GCG | GTG | CTG | CTA | GCC | TTC | CAT | 634 |
| Leu | Val | Leu | Leu | Thr | Ala | Val | Leu | Leu | Ala | Phe | His |
|     |     | 160 |     |     |     |     | 165 |     |     |     |     |

| GCT | GCA | CCT | GCC | CGC | CCT | CAG | CCT | GCC | TAC | GTG | GCC | 670 |
| Ala | Ala | Pro | Ala | Arg | Pro | Gln | Pro | Ala | Tyr | Val | Ala |
|     | 170 |     |     |     |     | 175 |     |     |     |     | 180 |

| CTG | CTG | GCC | TGT | GCC | GCC | ACC | CTC | TTC | GTG | GCG | CTC | 706 |
| Leu | Leu | Ala | Cys | Ala | Ala | Thr | Leu | Phe | Val | Ala | Leu |
|     |     |     |     | 185 |     |     |     |     | 190 |     |     |

| ATG | GTG | GTG | TGT | AAC | CGG | CAC | AGC | TTT | CGC | CAG | GAC | 742 |
| Met | Val | Val | Cys | Asn | Arg | His | Ser | Phe | Arg | Gln | Asp |
|     |     | 195 |     |     |     |     | 200 |     |     |     |     |

| TCC | ATG | TGG | GTG | GTG | AGC | TAC | GTG | GTG | CTG | GGC | ATC | 778 |
| Ser | Met | Trp | Val | Val | Ser | Tyr | Val | Val | Leu | Gly | Ile |
| 205 |     |     |     | 210 |     |     |     |     | 215 |     |     |

| CTG | GCA | GCC | GTT | CAG | GTT | GGG | GGT | GCC | CTG | GCA | GCC | 814 |
| Leu | Ala | Ala | Val | Gln | Val | Gly | Gly | Ala | Leu | Ala | Ala |
|     |     |     | 220 |     |     |     |     | 225 |     |     |     |

| AAC | CCC | CGC | AGC | CCC | TCT | GTG | GGC | CTC | TGG | TGC | CCT | 850 |
| Asn | Pro | Arg | Ser | Pro | Ser | Val | Gly | Leu | Trp | Cys | Pro |
|     | 230 |     |     |     |     | 235 |     |     |     |     | 240 |

| GTG | TTT | TTT | GTC | TAC | ATC | ACC | TAC | ACG | CTC | CTA | CCC | 886 |
| Val | Phe | Phe | Val | Tyr | Ile | Thr | Tyr | Thr | Leu | Leu | Pro |
|     |     |     |     |     | 245 |     |     |     | 250 |     |     |

| ATC | CGC | ATG | CGG | GCA | GCT | GTC | TTC | AGT | GGC | CTG | GGC | 922 |
| Ile | Arg | Met | Arg | Ala | Ala | Val | Phe | Ser | Gly | Leu | Gly |
|     |     | 255 |     |     |     |     | 260 |     |     |     |     |

| CTG | TCC | ACC | CTG | CAT | TTG | ATC | TTG | GCC | TGG | CAA | CTC | 958 |
| Leu | Ser | Thr | Leu | His | Leu | Ile | Leu | Ala | Trp | Gln | Leu |
| 265 |     |     |     |     | 270 |     |     |     |     | 275 |     |

| AAC | CGC | GGT | GAC | GCC | TTC | CTC | TGG | AAG | CAG | CTC | GGT | 994 |
| Asn | Arg | Gly | Asp | Ala | Phe | Leu | Trp | Lys | Gln | Leu | Gly |
|     |     |     | 280 |     |     |     |     | 285 |     |     |     |

| GCC | AAC | ATG | CTG | CTG | TTC | CTC | TGC | ACC | AAC | GTC | ATT | 1030 |
| Ala | Asn | Met | Leu | Leu | Phe | Leu | Cys | Thr | Asn | Val | Ile |
|     | 290 |     |     |     |     | 295 |     |     |     |     | 300 |

| GGC | ATC | TGC | ACA | CAC | TAC | CCA | GCT | GAG | GTC | TCT | CAG | 1066 |
| Gly | Ile | Cys | Thr | His | Tyr | Pro | Ala | Glu | Val | Ser | Gln |
|     |     |     |     | 305 |     |     |     |     | 310 |     |     |

| CGC | CAG | GCC | TTT | CAG | GAG | ACC | CGC | GGT | TAC | ATT | CAG | 1102 |
| Arg | Gln | Ala | Phe | Gln | Glu | Thr | Arg | Gly | Tyr | Ile | Gln |
|     |     |     | 315 |     |     |     |     | 320 |     |     |     |

| GCC | CGG | CTG | CAC | CTG | CCA | GAT | GAG | AAC | CGG | CAG | CAG | 1138 |
| Ala | Arg | Leu | His | Leu | Pro | Asp | Glu | Asn | Arg | Gln | Gln |
| 325 |     |     |     |     | 330 |     |     |     |     | 335 |     |

| GAA | CGG | CTG | CTG | CTG | TCC | GTG | TTG | CCC | CAG | CAT | GTT | 1174 |
| Glu | Arg | Leu | Leu | Leu | Ser | Val | Leu | Pro | Gln | His | Val |
|     |     |     |     | 340 |     |     |     |     | 345 |     |     |

| GCC | ATG | GAG | ATG | AAA | GAA | GAT | ATC | AAC | ACA | AAG | AAA | 1210 |
| Ala | Met | Glu | Met | Lys | Glu | Asp | Ile | Asn | Thr | Lys | Lys |
|     | 350 |     |     |     |     | 355 |     |     |     |     | 360 |

| GAA | GAC | ATG | ATG | TTC | CAC | AAG | ATC | TAC | ATC | CAG | AAG | 1246 |
| Glu | Asp | Met | Met | Phe | His | Lys | Ile | Tyr | Ile | Gln | Lys |
|     |     |     |     | 365 |     |     |     |     | 370 |     |     |

| CAT | GAC | AAT | GTC | AGC | ATC | CTG | TTT | GCA | GAC | ATT | GAA | 1282 |
| His | Asp | Asn | Val | Ser | Ile | Leu | Phe | Ala | Asp | Ile | Glu |
|     |     |     | 375 |     |     |     |     | 380 |     |     |     |

| GGC | TTC | ACC | AGC | CTG | GCG | TCC | CAG | TGC | ACC | GCG | CAG | 1318 |
| Gly | Phe | Thr | Ser | Leu | Ala | Ser | Gln | Cys | Thr | Ala | Gln |
| 385 |     |     |     |     | 390 |     |     |     |     | 395 |     |

| GAG | CTG | GTC | ATG | ACC | CTG | AAC | GAG | CTC | TTC | GCC | CGG | 1354 |

-continued

| | | | | | | | | | | |
|---|---|---|---|---|---|---|---|---|---|---|
| Glu | Leu | Val | Met<br>400 | Thr | Leu | Asn | Glu<br>405 | Leu | Phe | Ala | Arg |

| TTT | GAC | AAG | CTG | GCT | GCG | GAA | AAT | CAC | TGC | CTG | AGG | 1390 |
| Phe | Asp<br>410 | Lys | Leu | Ala | Ala | Glu<br>415 | Asn | His | Cys | Leu | Arg<br>420 | |

| ATC | AAG | ATC | TTA | GGG | GAC | TGT | TAC | TAC | TGT | GTG | TCG | 1426 |
| Ile | Lys | Ile | Leu<br>425 | Gly | Asp | Cys | Tyr | Tyr<br>430 | Cys | Val | Ser | |

| GGG | CTG | CCG | GAG | GCC | CGG | GCA | GAC | CAT | GCC | CAC | TGG | 1462 |
| Gly | Leu | Pro<br>435 | Glu | Ala | Arg | Ala | Asp<br>440 | His | Ala | His | Cys | |

| TGT | GTG | GAG | ATG | GGG | GTG | GAC | ATG | ATC | GAG | GCC | ATC | 1498 |
| Cys<br>445 | Val | Glu | Met | Gly<br>450 | Val | Asp | Met | Ile | Glu<br>455 | Ala | Ile | |

| TCG | CTG | GTG | CGT | GAG | GTG | ACA | GGT | GTG | AAC | GTG | AAC | 1534 |
| Ser | Leu | Val | Arg<br>460 | Glu | Val | Thr | Gly | Val<br>465 | Asn | Val | Asn | |

| ATC | CGC | GTG | GGC | ATC | CAC | AGC | GGG | CGT | GTG | CAC | TGT | 1570 |
| Met | Arg<br>470 | Val | Gly | Ile | His<br>475 | Ser | Gly | Arg | Val | His<br>480 | Cys | |

| GGT | GTC | CTT | GGC | CTG | CGG | AAA | TGG | CAG | TTC | GAC | GTG | 1606 |
| Gly | Val | Leu | Gly | Leu<br>485 | Arg | Lys | Trp | Gln | Phe<br>490 | Asp | Val | |

| TGG | TCC | AAT | GAC | GTG | ACT | CTG | GCC | AAC | CAT | ATG | GAG | 1642 |
| Trp | Ser | Asn | Asp<br>495 | Val | Thr | Leu | Ala | Asn<br>500 | His | Met | Glu | |

| GCG | GCC | CGG | GCC | GGC | CGC | ATC | CAC | ATC | ACC | CGG | GCC | 1678 |
| Ala | Ala | Arg<br>505 | Ala | Gly | Arg | Ile | His<br>510 | Ile | Thr | Arg | Ala<br>515 | |

| ACG | CTG | CAG | TAC | CTG | AAC | GGG | GAC | TAC | GAG | GTG | GAG | 1714 |
| Thr | Leu | Gln | Tyr<br>520 | Leu | Asn | Gly | Asp | Tyr<br>525 | Glu | Val | Glu | |

| CCG | GGC | CGC | GGT | GGC | GAG | CGG | AAC | GCG | TAC | CTC | AAG | 1750 |
| Pro | Gly | Arg<br>530 | Gly | Gly | Glu | Arg | Asn<br>535 | Ala | Tyr | Leu | Lys<br>540 | |

| GAG | CAG | CAC | ATC | GAG | ACC | TTC | CTC | ATC | CTG | GGA | GCC | 1786 |
| Glu | Gln | His | Ile | Glu<br>545 | Thr | Phe | Leu | Ile | Leu<br>550 | Gly | Ala | |

| AGC | CAG | AAA | CGG | AAA | GAG | GAG | AAG | GCC | ATG | CTG | GCC | 1822 |
| Ser | Gln | Lys | Arg<br>555 | Lys | Glu | Glu | Lys | Ala<br>560 | Met | Leu | Ala | |

| AAG | CTG | CAG | CGG | ACG | CGG | GCC | AAC | TCC | ATG | GAA | GGC | 1858 |
| Lys | Leu | Gln | Arg | Thr<br>570 | Arg | Ala | Asn | Ser | Met<br>575 | Glu | Gly | |
| 565 | | | | | | | | | | | | |

| CTG | ATG | CCA | CGC | TGG | GTG | CCC | GAC | CGC | GCC | TTC | TTC | 1894 |
| Leu | Met | Pro | Arg<br>580 | Trp | Val | Pro | Asp | Arg<br>585 | Ala | Phe | Ser | |

| CGG | ACC | AAG | GAC | TCC | AAG | GCT | TTC | CGC | CAG | ATG | GGC | 1930 |
| Arg | Thr<br>590 | Lys | Asp | Ser | Lys | Ala<br>595 | Phe | Arg | Gln | Met | Gly<br>600 | |

| ATT | GAT | GAT | TCC | AGC | AAA | GAC | AAC | CGG | GGT | GCC | CAA | 1966 |
| Ile | Asp | Asp | Ser | Ser<br>605 | Lys | Asp | Asn | Arg | Gly<br>610 | Ala | Gln | |

| GAT | GCC | CTG | AAC | CCC | GAG | GAT | GAG | GTC | GAT | GAG | TTC | 2002 |
| Asp | Ala | Leu<br>615 | Asn | Pro | Glu | Asp | Glu<br>620 | Val | Asp | Glu | Phe | |

| CTG | GGC | CGT | GGC | ATC | GAT | GCC | CGC | AGC | ATC | GAT | CAG | 2038 |
| Leu | Gly | Arg | Ala | Ile<br>630 | Asp | Ala | Arg | Ser | Ile<br>635 | Asp | Gln | |
| 625 | | | | | | | | | | | | |

| CTA | CGG | AAG | GAC | CAT | GTG | CGC | CGC | TTC | CTG | CTC | ACC | 2074 |
| Leu | Arg | Lys | Asp<br>640 | His | Val | Arg | Arg | Phe<br>645 | Leu | Leu | Thr | |

-continued

| | | | | | | | | | | |
|---|---|---|---|---|---|---|---|---|---|---|
| TTC | CAG | AGA | GAG | GAT | CTT | GAA | AAG | AAG | TAC | TCA | AGG | 2110 |
| Phe | Gln | Arg | Glu | Asp | Leu | Glu | Lys | Lys | Tyr | Ser | Arg | |
| 650 | | | | | 655 | | | | | | 660 | |

| AAG | GTG | GAC | CCC | CGC | TTC | GGA | GCC | TAC | GTG | GCC | TGT | 2146 |
| Lys | Val | Asp | Pro | Arg | Phe | Gly | Ala | Tyr | Val | Ala | Cys | |
| | | | | 665 | | | | | 670 | | | |

| GCG | CTG | TTG | GTC | TTC | TGC | TTC | ATC | TGC | TTT | ATC | CAG | 2182 |
| Ala | Leu | Leu | Val | Phe | Cys | Phe | Ile | Cys | Phe | Ile | Gln | |
| | | 675 | | | | | 680 | | | | | |

| CTC | CTC | GTC | TTC | CCA | CAC | TCA | ACC | GTG | ATG | CTT | GGG | 2218 |
| Leu | Leu | Val | Phe | Pro | His | Ser | Thr | Val | Met | Leu | Gly | |
| 685 | | | | | 690 | | | | | 695 | | |

| ATC | TAC | GCC | AGT | ATC | TTT | GTG | CTG | TTG | CTG | ATC | ACC | 2254 |
| Ile | Tyr | Ala | Ser | Ile | Phe | Val | Leu | Leu | Leu | Ile | Thr | |
| | | | 700 | | | | | 705 | | | | |

| GTG | CTG | ACC | TGT | GCC | GTG | TAC | TCC | TGT | GGC | TCT | CTC | 2290 |
| Val | Leu | Thr | Cys | Ala | Val | Tyr | Ser | Cys | Gly | Ser | Leu | |
| | 710 | | | | | 715 | | | | | 720 | |

| TTC | CCC | AAG | GCC | CTG | CGA | CGT | CTT | TCC | CGC | AGC | ATC | 2326 |
| Phe | Pro | Lys | Ala | Leu | Arg | Arg | Leu | Ser | Arg | Ser | Ile | |
| | | | | 725 | | | | | 730 | | | |

| GTC | CGC | TCT | CGG | GCA | CAC | AGC | ACT | GTG | GTT | GGC | ATT | 2362 |
| Val | Arg | Ser | Arg | Ala | His | Ser | Thr | Val | Val | Gly | Ile | |
| | | 735 | | | | | 740 | | | | | |

| TTT | TCA | GTC | TTG | CTA | GTG | TTC | ACC | TCT | GCC | ATC | GCC | 2398 |
| Phe | Ser | Val | Leu | Leu | Val | Phe | Thr | Ser | Ala | Ile | Ala | |
| 745 | | | | | 750 | | | | | 755 | | |

| AAC | ATG | TTC | ACC | TGT | AAC | CAC | ACC | CCC | ATC | CGG | ACC | 2434 |
| Asn | Met | Phe | Thr | Cys | Asn | His | Thr | Pro | Ile | Arg | Thr | |
| | | | 760 | | | | | 765 | | | | |

| TGT | GCA | GCC | CGG | ATG | CTG | AAT | GTA | ACA | CCC | GCT | GAC | 2470 |
| Cys | Ala | Ala | Arg | Met | Leu | Asn | Val | Thr | Pro | Ala | Asp | |
| | 770 | | | | | 775 | | | | | 780 | |

| ATC | ACT | GCC | TGC | CAC | CTG | CAG | CAG | CTC | AAT | TAC | TCT | 2506 |
| Ile | Thr | Ala | Cys | His | Leu | Gln | Gln | Lys | Asn | Tyr | Ser | |
| | | | | 785 | | | | | 790 | | | |

| CTG | GGC | CTG | GAT | GCT | CCG | CTG | TGT | GAG | GGC | ACC | GCA | 2542 |
| Leu | Gly | Leu | Asp | Ala | Pro | Leu | Cys | Glu | Gly | Thr | Ala | |
| | | 795 | | | | | 800 | | | | | |

| CCC | ACT | TGC | AGC | TTC | CCT | GAG | TAC | TTC | GTT | GGG | AAC | 2578 |
| Pro | Thr | Cys | Ser | Phe | Pro | Glu | Tyr | Phe | Val | Gly | Asn | |
| 805 | | | | | 810 | | | | | 815 | | |

| ATG | CTG | CTG | AGT | CTC | TTG | GCC | AGC | TCT | GTT | TTC | CTG | 2614 |
| Met | Leu | Leu | Ser | Leu | Leu | Ala | Ser | Ser | Val | Phe | Leu | |
| | | | 820 | | | | | 825 | | | | |

| CAC | ATC | AGT | AGC | ATC | GGG | AAG | TTG | GCC | ATG | ATC | TTT | 2650 |
| His | Ile | Ser | Ser | Ile | Gly | Lys | Leu | Ala | Met | Ile | Phe | |
| | 830 | | | | | 835 | | | | | 840 | |

| GTC | CTG | GGG | GTC | ATT | TAT | TTG | GTG | CTG | CTT | CTG | CTG | 2686 |
| Val | Leu | Gly | Leu | Ile | Tyr | Leu | Val | Leu | Leu | Leu | Leu | |
| | | | | 845 | | | | | 850 | | | |

| GGC | CCC | CCC | AGC | ACC | ATC | TTT | GAC | AAC | TAT | GAC | CTG | 2722 |
| Gly | Pro | Pro | Ser | Thr | Ile | Phe | Asp | Asn | Tyr | Asp | Leu | |
| | | 855 | | | | | 860 | | | | | |

| CTG | CTT | GGT | GTC | CAT | GGC | TTG | GCT | TCT | TCC | AAT | GAC | 2758 |
| Leu | Leu | Gly | Val | His | Gly | Leu | Ala | Ser | Ser | Asn | Asp | |
| 865 | | | | | 870 | | | | | 875 | | |

| ACC | TTT | GAT | GGG | CTG | GAC | TGC | CCA | GCT | GCG | GGG | AGG | 2794 |
| Thr | Phe | Asp | Gly | Leu | Asp | Cys | Pro | Ala | Ala | Gly | Arg | |
| | | | 880 | | | | | 885 | | | | |

| GTG | GCA | CTG | AAA | TAC | ATG | ACC | CCT | GTG | ATT | CTG | CTG | 2830 |

-continued

| | | | | | | | | | | | |
|---|---|---|---|---|---|---|---|---|---|---|---|
| Val | Ala | Leu | Lys | Tyr | Met | Thr | Pro | Val | Ile | Leu | Leu |
| | | | 890 | | | 895 | | | | | 900 |

```
GTG TTT GCC CTG GCG CTG TAT CTG CAC GCC CAG CAG        2866
Val Phe Ala Leu Ala Leu Tyr Leu His Ala Gln Gln
                905                 910

GTG GAA TCA ACT GCA CGT CTG GAC TTC CTC TGG AAA        2902
Val Glu Ser Thr Ala Thr Leu Asp Phe Leu Trp Lys
        915                 920

CTG CAG GCA ACG GGG GAG AAG GAG GAG ATG GAG GAG        2938
Leu Gln Ala Thr Gly Glu Lys Glu Glu Met Glu Glu
925             930                 935

CTC CAG GCC TAC AAC CGA AGG CTG CTG CAT AAC ATT        2974
Leu Gln Ala Tyr Asn Arg Arg Leu Leu His Asn Ile
            940                 945

CTG CCT AAG GAC GTG GCT GCC CAC TTC CTG GCC CGG        3010
Leu Pro Lys Asp Val Ala Ala His Phe Leu Ala Arg
950                 955                 960

GAG CGC CGG AAC GAT GAG CTC TAC TAC CAG TCG TGT        3046
Glu Arg Arg Asn Asp Glu Leu Tyr Tyr Gln Ser Cys
                965                 970

GAG TGT GTG GCC GTC ATG TTT GCC TCC ATT GCC AAC        3082
Glu Cys Val Ala Val Met Phe Ala Ser Ile Ala Asn
        975                 980

TTT TCT GAG TTC TAT GTG GAG CTG GAG GCA AAC AAT        3118
Phe Ser Glu Phe Tyr Val Glu Leu Glu Ala Asn Asn
985             990                 995

GAG GGT GTC GAG TGC CTG CGG CTG CTC AAC GAA ATC        3154
Glu Gly Val Glu Cys Leu Arg Leu Leu Asn Glu Ile
            1000                1005

ATC GCC GAC TTT GAT GAG ATC ATC AGC GAG GAG CGG        3190
Ile Ala Asp Phe Asp Glu Ile Ile Ser Glu Glu Arg
1010                1015                1020

TTC CGG CAG CTG GAG AAA ATC AAG ACG ATC GGT AGC        3226
Phe Arg Gln Leu Glu Lys Ile Lys Thr Ile Gly Ser
                1025                1030

ACG TAC ATG GCT GCG TCG GGG CTG AAC GCC AGC ACC        3262
Thr Tyr Met Ala Ala Ser Gly Leu Asn Ala Ser Thr
        1035                1040

TAC GAT CAG GCC GGC CGC TCC CAC ATC ACT GCC CTG        3298
Tyr Asp Gln Ala Gly Arg Ser His Ile Thr Ala Leu
1045                1050                1055

GCC GAC TAT GCC ATG CGG CTC ATG GAG CAG ATG AAA        3334
Ala Asp Tyr Ala Met Arg Leu Met Glu Gln Met Lys
            1060                1065

CAC ATC AAC GAG CAC TCC TTC AAC AAC TTC CAG ATG        3370
His Ile Asn Glu His Ser Phe Asn Asn Phe Gln Met
    1070                1075                1080

AAG ATT GGG CTG AAC ATG GGC CCA GTT GTG GCA GGC        3406
Lys Ile Gly Leu Asn Met Gly Pro Val Val Ala Gly
                1085                1090

GTC ATT GGG GCT CGG AAG CCA CAG TAT GAC ATC TGG        3442
Val Ile Gly Ala Arg Lys Pro Gln Tyr Asp Ile Trp
        1095                1100

GGG AAC ACG GTG AAT GTC TCT AGC CGT ATG GAC AGC        3478
Gly Asn Thr Val Asn Val Ser Ser Arg Met Asp Ser
1105                1110                1115

ACG GGG GTT CCT GAC CGA ATC CAG GTG ACC ACG GAC        3514
Thr Gly Val Pro Asp Arg Ile Gln Val Thr Thr Asp
            1120                1125

TTG TAC CAG GTT CTA GCT GCC AAA CGG TAC CAG CTG        3550
Leu Tyr Gln Val Leu Ala Ala Lys Arg Tyr Gln Leu
1130                1135                1140
```

| | | |
|---|---|---|
| GAG TGT CGA GGG GTG GTC AAG GTG AAG GGC AAG GGG<br>Glu Cys Arg Gly Val Val Lys Val Lys Gly Lys Gly<br>1145　　　　　　　　　1150 | | 3586 |
| GAG ATG ACC ACC TAC TTC CTC AAT GGG GGC CCC CCC<br>Glu Met Thr Thr Tyr Phe Leu Asn Gly Gly Pro Pro<br>　　　1155　　　　　　　　1160 | | 3622 |
| AGT TAG<br>Ser Xaa<br>1165 | | 3628 |
| CAGAGCCCAG | CTACAAGTTC AGCTGTCAGG ACCAAGGTGG | 3668 |
| GCATTTAAGT | GGACTCTGTG CTCGCTGGAT GGAGCTGTGG | 3708 |
| CCGGGGGCAC | CAAGCCTCCA GACCCTGCTG ACCACAAAAG | 3748 |
| GGAACACCTC | AGCAGGCTGT GCTTGGACCA TGCTCGTCTG | 3788 |
| CCCTCAGGCT | GGTGAACAAG GGATACCAAG AGGATTATGC | 3828 |
| AAGTGACTTT | TACTTTCTA ATTGGGGTAG GGCTGGCTGT | 3868 |
| TCCCTCTTTC | TTCCTGCTTT TGGGAGCAGG GGAGGCAGCT | 3908 |
| GCAGCAGAGG | CAGCAGGAGC CCTCCTGCCT GAGGGTTTAA | 3948 |
| AATGGCAGCT | TGCCATGCCT ACCCTTTCCC CTGTCTGTCT | 3988 |
| GGGCAACAGC | ATCGGGGCTG GGCCCTTCCT TTCCCTCTTT | 4028 |
| TTCCTGGGAA | TATTTGT | 4046 |